(12) United States Patent
Snyder

(10) Patent No.: US 6,969,394 B2
(45) Date of Patent: Nov. 29, 2005

(54) GUIDES TO PREVENT TANGLING SUTURES

(75) Inventor: Stephen J. Snyder, Encino, CA (US)

(73) Assignee: Linvatec Corporation, Largo, FL (US)

( * ) Notice: Subject to any disclaimer, the term of this patent is extended or adjusted under 35 U.S.C. 154(b) by 406 days.

(21) Appl. No.: 10/109,467

(22) Filed: Mar. 28, 2002

(65) Prior Publication Data

US 2003/0187466 A1 Oct. 2, 2003

(51) Int. Cl.[7] ............................................. A61B 17/04
(52) U.S. Cl. ...................................... 606/148; 289/17
(58) Field of Search ......................... 606/74, 113, 139, 606/148, 232, 103; 289/13, 15, 7; 206/364–366

(56) References Cited

U.S. PATENT DOCUMENTS

| | | | |
|---|---|---|---|
| 2,588,589 A * | 3/1952 | Tauber | 606/148 |
| 3,768,635 A * | 10/1973 | Eggert | 206/366 |
| 4,128,100 A * | 12/1978 | Wendorff | 606/74 |
| 4,185,636 A * | 1/1980 | Gabbay et al. | 606/148 |
| 4,732,150 A * | 3/1988 | Keener Jr. | 606/113 |
| 5,201,741 A * | 4/1993 | Dulebohn | 606/113 |
| 5,591,177 A * | 1/1997 | Lehrer | 606/139 |
| 5,669,917 A * | 9/1997 | Sauer et al. | 606/139 |
| 6,245,078 B1 * | 6/2001 | Ouchi | 606/113 |

* cited by examiner

Primary Examiner—Julian W. Woo
(74) Attorney, Agent, or Firm—Gene Warzecha

(57) ABSTRACT

A suture management system useful in endoscopic surgery, particularly in arthroscopic instability and rotator cuff procedures comprises a plurality of elongated tubes, sometimes referred to herein as suture organizers. The tubes can have a suture loop through them to ensnare matching suture ends of a given suture so that the tube can be slid down over the matching suture ends and into a cannula. The tube with the matched suture ends can be clamped over the suture strands to fixate the tube as another suture is manipulated through the tissue and then in turn has its matching suture ends pulled through another tube for subsequent tie-off. A rack is provided to hold the tubes with loops therein before use.

12 Claims, 6 Drawing Sheets

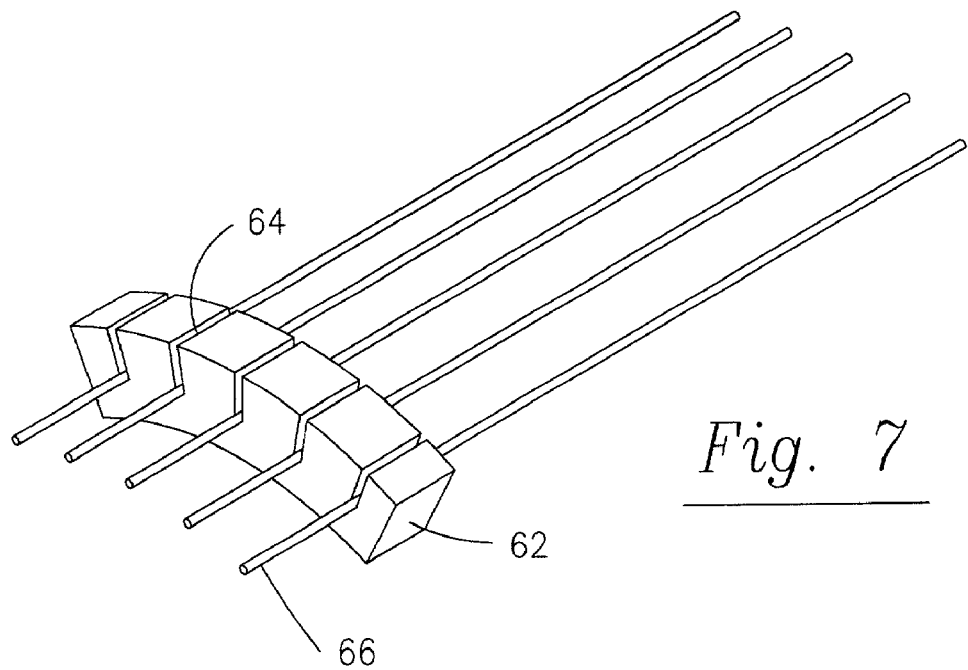
Fig. 7
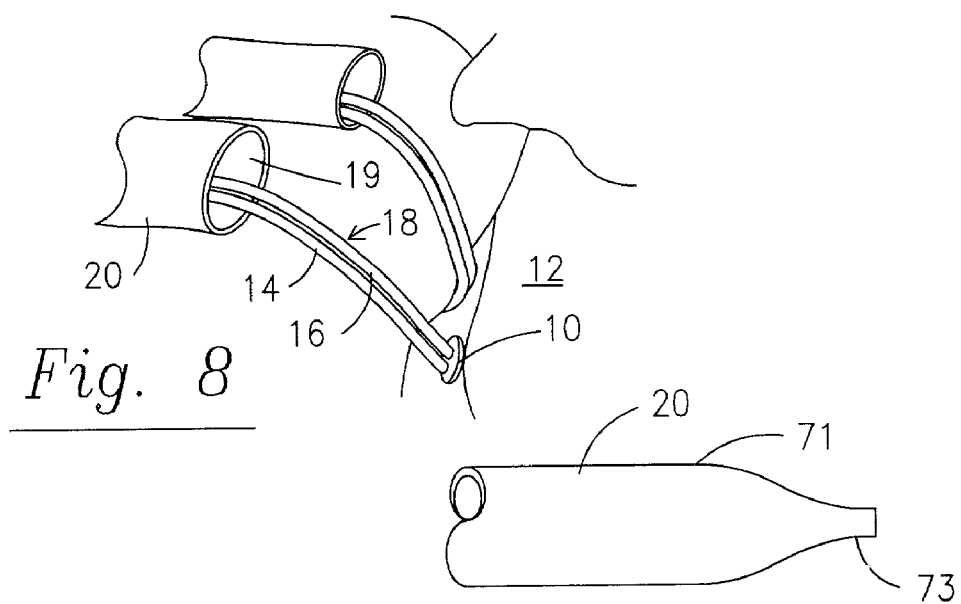
Fig. 8
Fig. 9

GUIDES TO PREVENT TANGLING SUTURES

BACKGROUND OF THE INVENTION

1. Field of the Invention

The field of this invention is surgical procedures, particularly endoscopic surgical procedures, involving the use of multiple sutures and devices to keep suture strands bundled until tied to prevent tangling.

2. Description of the Prior Art

Endoscopic surgery and, in particular, arthroscopic surgery often involves working in confined spaces while trying to embed suture anchors, penetrate soft tissue and tie off sutures. It will be understood that, generally, a suture extends through an eyelet at the proximal end of an anchor (embedded in bone) such that the suture is folded back on itself at some point between the suture ends. The part of the suture at which it is folded back on itself will sometimes be referred to herein as the bight portion. At least one of the ends is passed through tissue and is tied to the other end to anchor the tissue. Certain procedures such as rotator cuff and instability require numerous sutures, which sometimes are not tied off after being placed through tissue. The need to delay tying-off occurs to enhance visibility at a crowded work site and because subsequent sutures are more easily placed if previous adjacent sutures are not tied off at that time. The problem that occurs, without the present invention, is the management of associated pairs of suture ends for ultimate tying-off. While different colors can be used for sutures to distinguish them on a scope, the confined space and the limit of the colors available make it difficult to match two ends of a given suture that may be intertwined with ends of an unrelated suture.

When repairing rotator cuffs, anchors are placed in the bone, sometimes as many as five, and each suture (attached to a given anchor) has its ends taken out the cannula to be tied at the end of the operation. This technique has the benefit of not closing the torn tendon down to bone too early or too tightly, thereby making it easier to pass the stitching tool under the tendon. Larger anchors have been developed, doubling the number of sutures to manage since each anchor can accommodate two sutures. With larger suture anchors having so many sutures, it is difficult to wait until the end of the procedure before tying the sutures. A technique was developed to allow tying the sutures throughout the surgery. Although this technique worked well, it had two major drawbacks. First, once a suture is tied down it is more difficult to pass the rest of the stitches. Also, each time a pair of suture ends is passed the surgeon has to turn off the pump, move the scope, turn the pump back on, clean the blood out of the bursa and then tie the next set of sutures. It would save time and be much more efficient if the sutures could all be tied at once, at the end of the case. Without the present invention, it is difficult to wait to the end of the case because management of suture end pairs for proper tie-off is difficult.

In addition to managing sutures during rotator cuff surgery, there was also a need to manage them while doing instability surgery. During that operation two or three sutures are placed in the back of the shoulder at the beginning of a case but are not tied until the end of the case. When the anterior portion of the reconstruction is finished and the surgeon returns to the back of the shoulder to tie the suture, it is often difficult to determine which suture pairs go together, since there are four to six sutures present coming out of the portal. Sometimes the suture strands are twisted one on the other, making for a very confusing situation.

In the past, sutures were packaged in multi-suture holders but these products merely organized discrete sutures until the surgeon needed them in a procedure. Examples of such suture packaging are shown in U.S. Pat. Nos. 5,123,528; 5,413,214; 5,848,714 and 5,566,822. These devices had no suture management capabilities when the sutures were taken out and used in a procedure (in an anchor, for example). Somewhat more relevant were anastomosis catheters which separated individual sutures until a suture needle was pushed out of a respective slot in the catheter to grab the tissue (for example, urethra). Examples of such devices are U.S. Pat. Nos. 5,545,171 and 6,080,167. These devices were designed with a specific procedure in mind and had to have all the sutures organized in discrete passages before the catheter was inserted in the patient. They were not adapted to manage untied sutures during a procedure that needed to be tied off at a later time.

An objective of the present invention is to simply provide such a suture management system to avoid mix-ups of unmatched pairs of sutures being tied together. Another objective is to have the suture organizers assembled in a rack and to provide them in a variety of colors to make them readily accessible and distinguishable on a scope.

SUMMARY OF THE INVENTION

These and other objects of the invention are achieved by the preferred embodiment disclosed herein which is a suture management system useful in arthroscopic surgery, particularly in instability and rotator cuff procedures. The system comprises a plurality of elongated tubes, sometimes referred to herein as suture organizers. The tubes can have a suture loop through them to facilitate placing the suture through the tube by ensnaring matching suture ends of a given suture so that the tube can be slid down over the matching (associated) suture ends and into a cannula. The tube with the matched suture ends can be clamped onto the suture strands to fixate the tube so another suture can be manipulated through the tissue and then in turn have its matching suture ends pulled through another tube for subsequent tie-off. A rack is provided to hold the tubes with loops therein before use.

BRIEF DESCRIPTION OF THE DRAWINGS

FIGS. 5–7 show variations of racks to hold suture organizers prior to use.

FIG. 8 shows the use of a suture organizer in place in rotator cuff surgery.

FIG. 9 shows an alternate embodiment of a suture organizer.

DESCRIPTION OF THE PREFERRED EMBODIMENT

Figure 1:
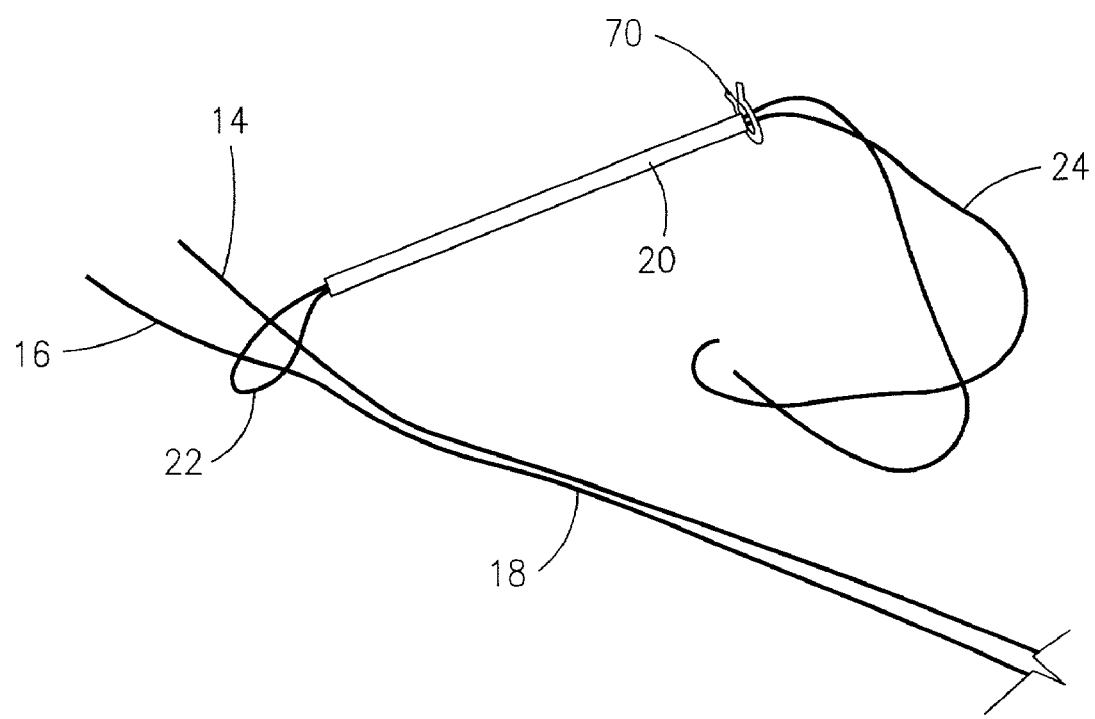
FIG. 1 shows a suture organizer with a loop inserted into it ready to grasp matching ends of a suture shown before the tube is advanced through a cannula.

FIG. 8 shows an application of the present invention to rotator cuff surgery. While the invention is described in terms of an arthroscopic shoulder procedure, as will be understood below, the invention is suitable for other endoscopic procedures and for open surgical procedures. A suture anchor 10 is secured in a known manner to the bone 12. Ends 14 and 16 extend from the bight portion of suture 18 and from anchor 10. A suture organizer 20 is slipped over ends 14 and 16 before they are tied off. Insertion of the suture ends 14 and 16 into tube 20 is shown in FIG. 1 with the use of a threading tool comprising a loading suture 24 folded into a collapsible loop 22 which extends out of distal end 26 of organizer 20. Ends 14 and 16 of suture 18 are inserted into loop 22 and loop 22 is pulled through the lumen 19 of organizer 20. Alternatively, loop 22 may be provided in the form of a rod (not shown) extending through the lumen of the organizer 20 and having at its distal end a collapsible loop of shape memory material such as nitinol. The organizer 20 is pushed along suture ends 14 and 16 toward the work site and through a cannula, such as for example 28 shown for an instability procedure in FIG. 2.

Figure 2:
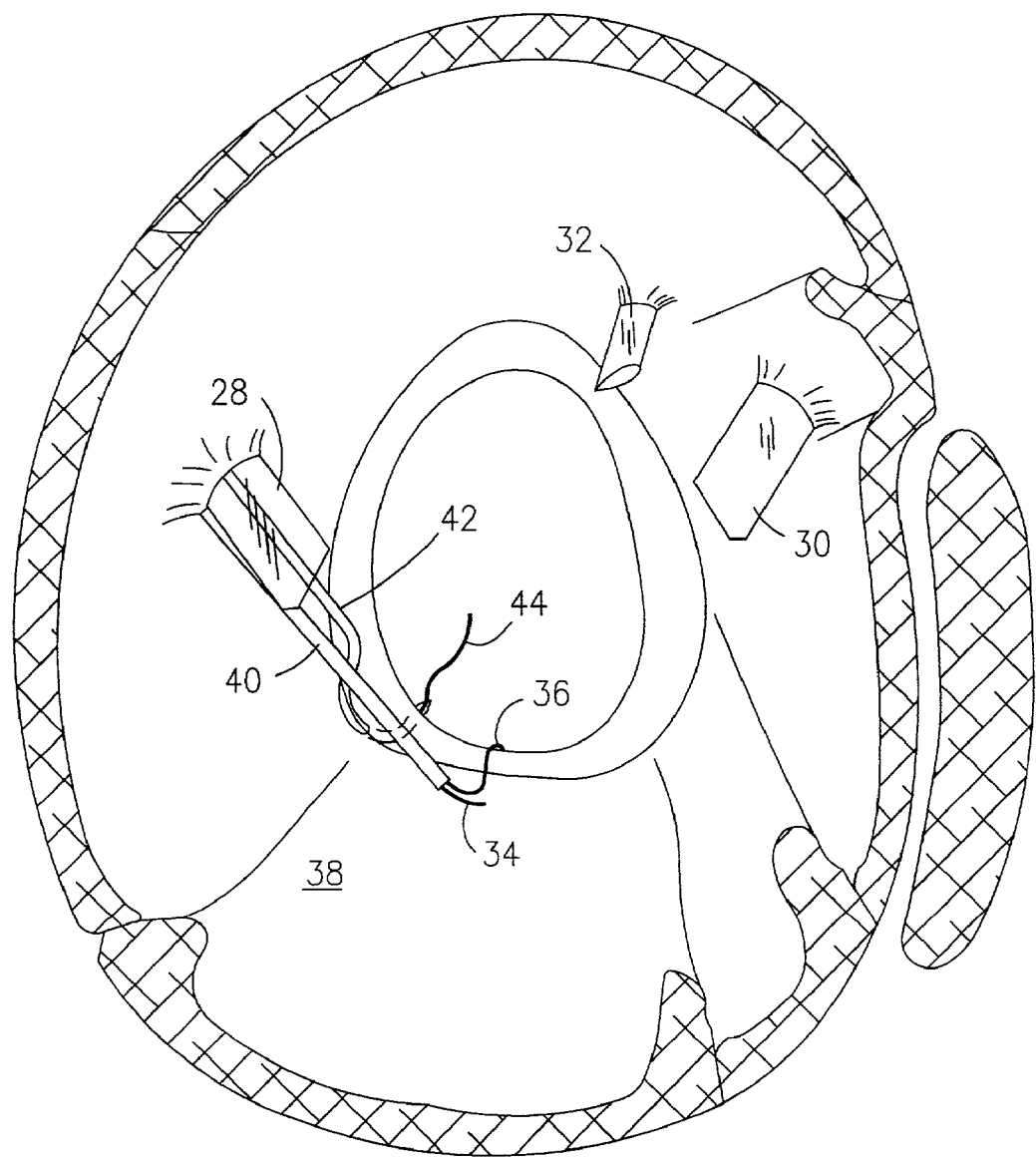
FIG. 2 shows the use of the suture organizers in an instability procedure.
Figure 3:
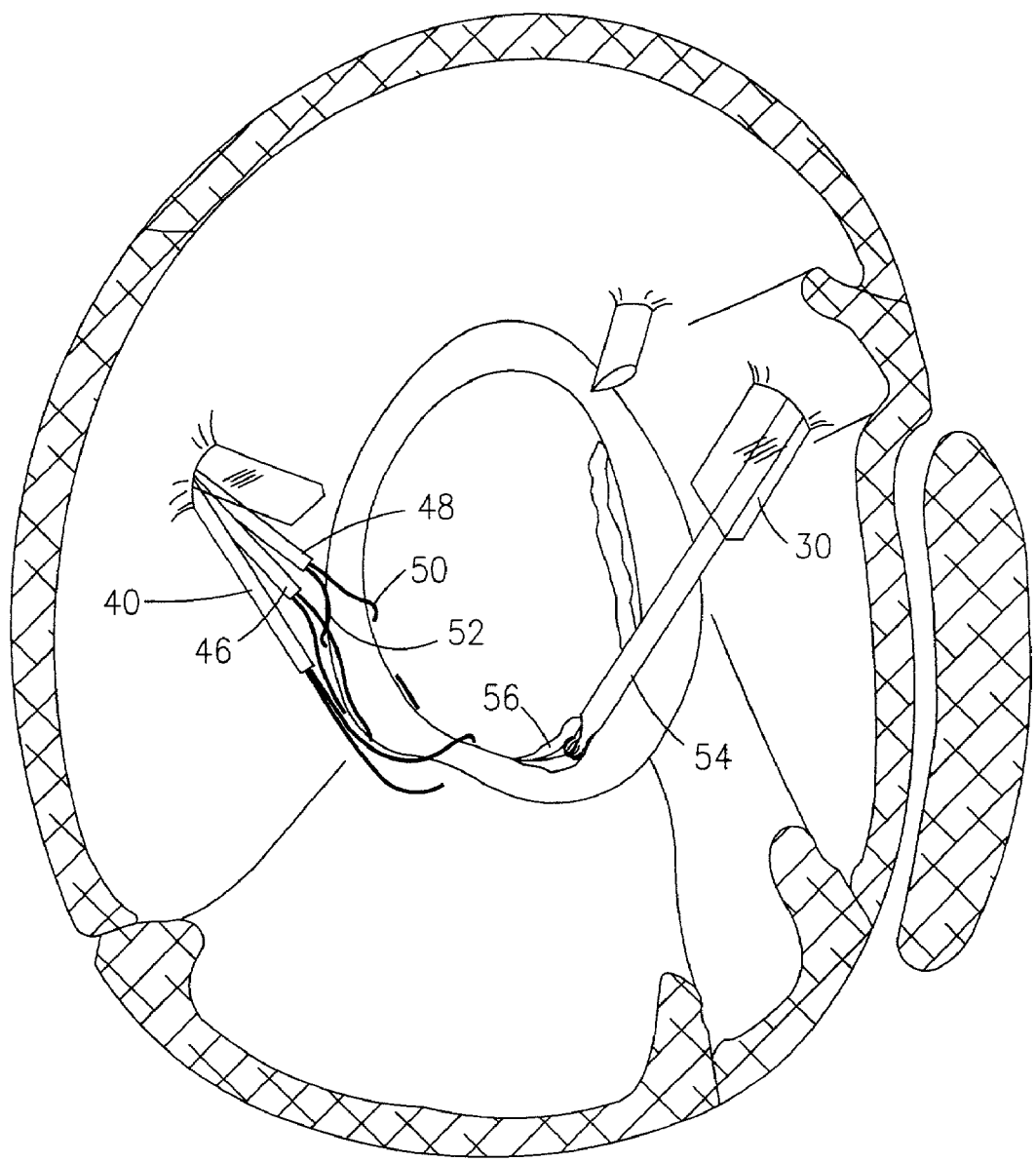
FIG. 3 is a view of FIG. 2 later in the procedure showing the use of multiple suture organizers.
Figure 4:
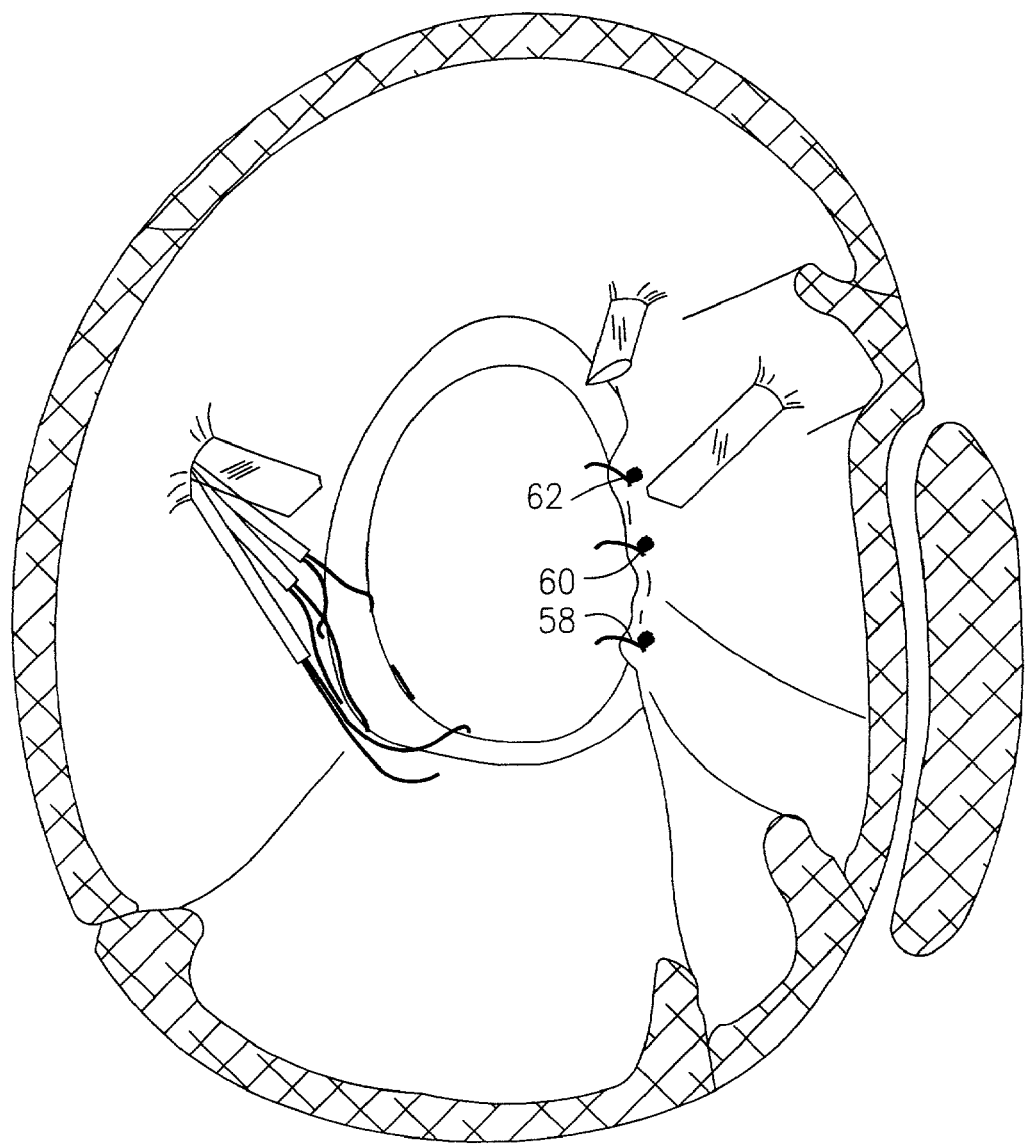
FIG. 4 is a view of FIG. 3 later in the procedure showing one side tied off and the suture organizers on the opposite side holding suture ends together prior to tying-off.

Regardless of the type of surgery being performed, the procedure of using the organizers is similar. A suture can be anchored to bone as shown in FIG. 8 and left to be tied later in the procedure while an organizer 20 holds the respective ends such as 14 and 16 as a matched pair. FIGS. 2–4 show an instability surgery but do not show the anchors holding the various sutures described below. Cannulas 28 and 30 provide access to the site through small incisions made in the patient. Another incision allows for the insertion of a combination light and scope 32 to allow the site to be viewed by the surgeon on a monitor (not shown). In FIG. 2, suture ends 34 and 36 have been sewn through tissue 38 and an organizer 40 has been run down ends 34 and 36 from outside cannula 28. A hollow suture needle 42 holding suture 44 has been inserted through the tissue 38. After removal of the needle, the ends of suture 44 will be routed through organizer 46, as shown in FIG. 3. Yet another organizer 48 holds suture ends 50 and 52 of yet another suture that is subsequently sewn. FIG. 3 shows a surgical bur 54 inserted through cannula 30 to prepare the bone 56 for the conclusion of the instability procedure. FIG. 4 shows that sutures 58, 60 and 62 have been sewn through the tissue 38 and tied off with the excess already removed. Subsequently, each pair of suture ends can be brought through the cannula 28 at which time the particular organizer associated with the suture ends can be removed and several knots can be pushed down to tie one suture pair at a time while the remaining untied sutures have their end pairs held together and out of the way by their respective organizers. Each of the organizers can be held in position outside the patient by being clamped on the suture ends extending through it, after the organizer is fully advanced. Such clamping could be accomplished by a separate clamp 70 (FIG. 1) or by a simple forceps tool (not shown) or by forming the proximal end 71 of the organizer into a smaller diameter or crimped end 73 to frictionally engage the suture (best seen in FIG. 9). Each organizer can also serve as a guide for insertion of a cannula, if needed during the procedure. This can be done just prior to tying off a pair of suture ends by grasping the organizers and directing them out, one at a time through the cannula. Using this procedure avoids confusion and assures that proper suture ends are tied.

Figure 5:
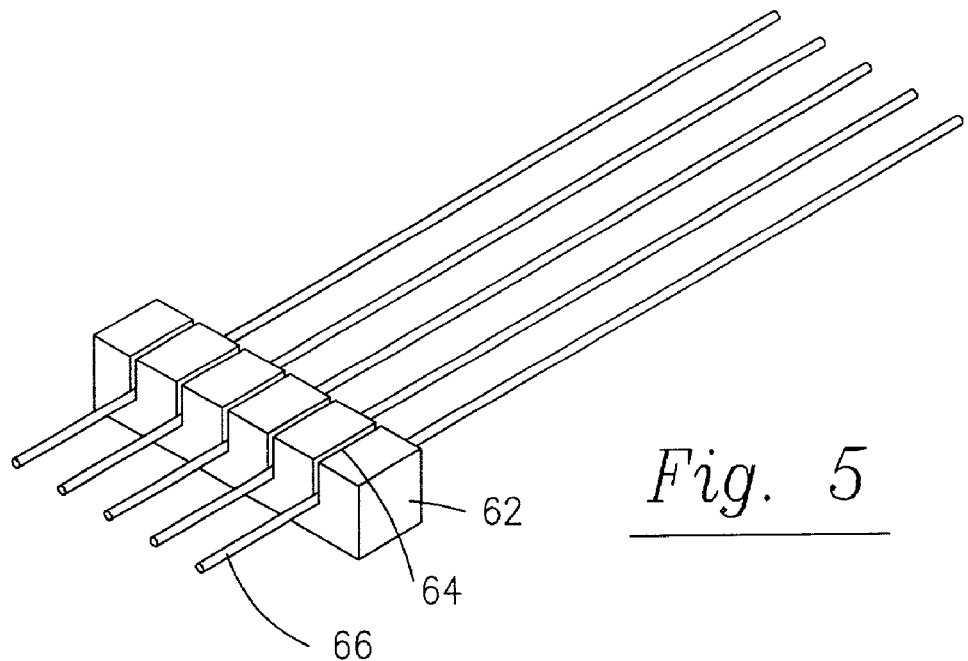
Figure 6:
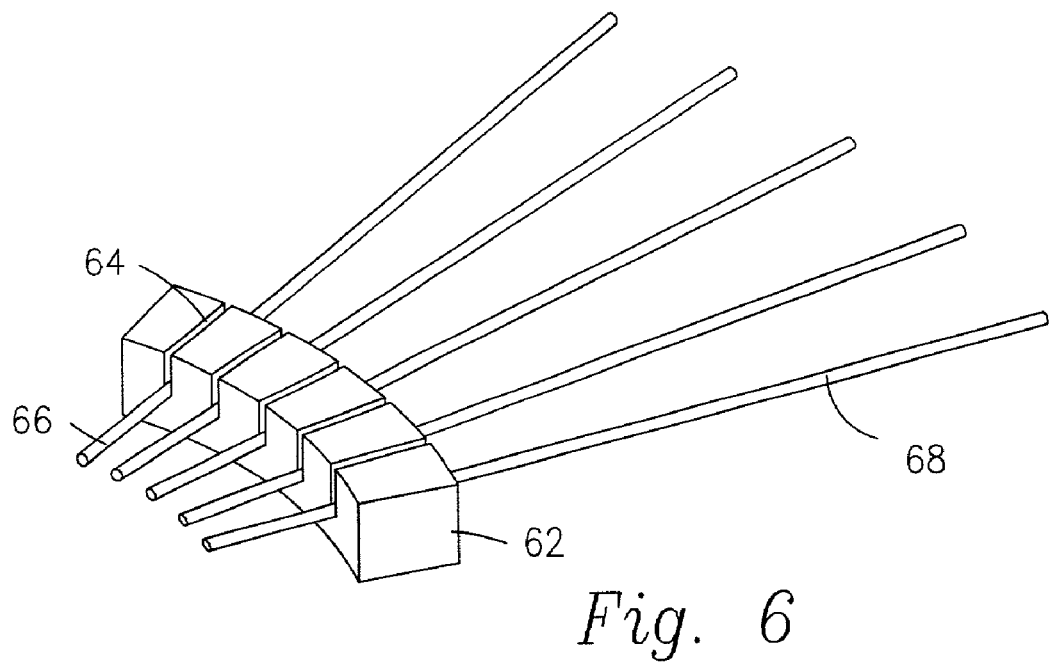

For shoulder arthroscopic procedures the organizers should be in the range of 5 to 9 inches (12.7 to 22.86 cm) and preferably about 7 inches (17.78 cm) long. They can vary in diameter, although an outside diameter of about 0.083 inches (2.1 mm) and an inside diameter of about 0.063 inches (1.6 mm) (i.e. about the size found in a 14 gauge angiocatheter) is preferred for two strands of #2 suture. The inside diameter (lumen) of a 12 gauge catheter would be suitable for #5 suture. Various lengths and diameters (6 to 22 gauge, for example) may be used depending upon the procedure and surgeon preference. The organizers should preferably be made of biocompatible plastic and need to be reasonably rigid to facilitate use, handling and storage whether or not a rack such as rack 62 is used as shown in FIGS. 5–7. The rack 62 can be a rectangular block with slots 64 into which the organizers 66 can be snapped or otherwise received, and placed in a sterile package. The curvature in the embodiment of FIG. 6 allows the ends 68 to be further apart for simpler grasping. Optionally, as shown in FIG. 7, the curvature of the rack 62 can be about a line parallel to the plane of curvature shown in FIG. 6, so as to preserve the parallel alignment of the organizers.

The length of organizers in a set or kit can vary to address the need of the particular application. The organizers can be produced in different colors to more easily distinguish them and to insure the desired organizer has in fact been grasped. The lumen size can be varied. More than two ends of a single suture could be run through a single organizer. For example, a particular anchor may fixate two sutures of different colors with the two pairs of ends extending through a single organizer. In that situation the color is used to insure the correct pair get tied together and the remaining pair gets tied immediately thereafter. Depending upon the parameters ultimately selected, the suture organizers could also be used in open surgical procedures, whether or not suture anchors are used.

Each organizer can be individually sheathed to maintain it in a sterile condition, whether packed individually or in sets in a rack 62. Each organizer is preferably packaged with a loop 22 extending from one end and a small clip 70, shown schematically in FIG. 1, and constructed similarly to a clamp on an intravenous drip. A series of protrusions on the exterior of the organizer can keep the clip 70 from falling off when not in the clamped position around a pair of suture ends to fixate the organizer. Clearly such a clamp is unnecessary if one uses an embodiment such as that shown in FIG. 9 (a restricted end).

While organizers 20 have been shown as having a single lumen 19 for accommodating a pair of suture ends, it will be understood that such organizers could have one lumen per suture end. Such a single lumen organizer used for a single suture end would double the number of organizers for a given procedure and, therefore, may not be suitable for certain applications even though it would ensure no tangling of sutures. Alternatively, an organizer could be provided with two or more lumens: one lumen for each suture end. Each lumen could be provided with its own threading tool. Using multi-lumen tubes one could accommodate various numbers of sutures within a single tube.

Depending upon the rigidity of the organizers, it may be desirable to utilize a supplemental tubular support (not shown) of greater rigidity. The supplemental support could be used temporarily by receiving within its lumen an organizer to thereby hold the organizer and its suture fairly straight to enable them to be easily passed through a cannula (in a portal during an arthroscopic shoulder procedure, for example).

It will be understood by those skilled in the art that numerous improvements and modifications may be made to the preferred embodiment of the invention described herein without departing from the spirit and scope thereof.

What is claimed is:

1. A method of performing a surgical procedure involving a plurality of associated pairs of ends of discrete sutures that need to be tied off after they have been sewn in place, each of said sutures folded back on itself to form a bight portion from which said ends extend comprising:

placing a first suture in a predetermined position in the patient;

forming a bight in said first suture;

bringing the ends of the suture extending from said bight out of the patient;

running a tube over said suture ends to separate said suture ends from other suture ends;

removing said tube from said suture ends prior to tying a knot with said suture ends.

2. The method of claim 1 further comprising:
placing a second suture in position in the patient;
bringing a second pair of suture ends out of the patient; and
running a second tube over said second pair of suture ends to prevent pairing said second suture ends with said first suture ends.

3. The method of claim 2 further comprising:
placing a tube on each pair of ends on a suture to be tied at a later point in the procedure than when it is placed;
inserting a cannula over a single tube before removing said tube;
tying the only pair of ends extending through said cannula to avoid confusion with other suture end pairs which extend through other tubes that are outside the cannula.

4. The method of claim 2 further comprising:
using a plurality of tubes to segregate end pairs of discrete sutures.

5. The method of claim 4 further comprising:
using a plurality of colors for said tubes.

6. The method of claim 2 further comprising:
using a plurality of suture colors;
inserting at least two pairs of color distinct suture end pairs in a single tube.

7. The method of claim 1 further comprising:
clamping said tube onto the suture ends running therethrough to selectively fixate said tube.

8. The method of claim 1 further comprising:
providing a preformed collapsible loop initially in said tube;
inserting the suture end pair into said loop;
pulling said loop with said suture end pair through said tube.

9. The method of claim 1 further comprising:
providing a rack to hold a plurality of said tubes.

10. The method of claim 9 further comprising:
snapping in a tube into a respective groove in said rack.

11. The method of claim 10 further comprising:
using a block shape for said rack.

12. The method of claim 11 further comprising:
providing a curvature to said rack.

* * * * *